US005700961A

United States Patent [19]

Anthony et al.

[11] Patent Number: 5,700,961
[45] Date of Patent: Dec. 23, 1997

[54] SYSTEM AND METHOD FOR MEASURING STICKINESS OF MATERIALS SUCH AS COTTON

[75] Inventors: William S. Anthony, Greenville; Richard K. Byler, Stoneville, both of Miss.

[73] Assignee: The United States of America as represented by the Secretary of Agriculture, Washington, D.C.

[21] Appl. No.: 666,769

[22] Filed: Jun. 19, 1996

[51] Int. Cl.[6] .................................................. G01N 33/36
[52] U.S. Cl. ........................... 73/866; 73/73; 324/694; 250/339.1; 250/339.11; 250/341.8; 422/82.02; 422/82.05
[58] Field of Search ............... 73/73, 54.22, 866, 73/159; 324/694, 695, 696, 722; 356/36, 244, 945, 245; 250/339.11, 576, 573, 341.8, 339.1; 422/82.02, 82.05; 19/66 CC

[56] References Cited

U.S. PATENT DOCUMENTS 4,458,528  7/1984  Roper et al. .......................... 73/152.48
5,087,120  2/1992  Anthony .................................. 356/36
5,125,279  6/1992  Anthony et al. ......................... 73/866
5,311,768  5/1994  Seib et al. ............................. 73/54.22

OTHER PUBLICATIONS

Byler, R.K. "Resistance–Moisture Content Relationship For Cotton Lint"—1992 Proceedings Beltwide Cotton Conference, pp. 1389–1392.
Byler, R.K. "Cotton Lint Moisture Measurement and Control in the Gin," The American Society of Agricultural Engineers, Paper No. 923032.

Primary Examiner—Hezron E. Williams
Assistant Examiner—Nashmiya Ashraf
Attorney, Agent, or Firm—M. Howard Silverstein; Joseph A. Lipovsky; John D. Fado

[57] ABSTRACT

A system and method for measuring the stickiness of agricultural solids such as cotton is provided. A reference moisture level of a sample is measured in a manner not responsive to the presence of sugars. The sugar-based moisture content of the sample is measured by sensors responsive to the presence of sugars. The difference between the reference moisture level and the sugar-based moisture content provides a measure of the relative stickiness of the sample.

16 Claims, 7 Drawing Sheets

SYSTEM AND METHOD FOR MEASURING STICKINESS OF MATERIALS SUCH AS COTTON

BACKGROUND OF THE INVENTION

1. Field of the Invention

The present invention relates generally to systems for grading or analyzing agricultural solids such as cotton. More particularly, the present invention relates to a system and method for measuring the stickiness of cotton.

2. Related Art

Cotton yield, as well as cotton processibility at the gin and textile mill, are severely degraded by the presence of sticky, sugary deposits produced by insects that feed on the cotton plant. These concentrated sugary insect deposits, often referred to as "honeydew", are most commonly produced as secretions by whiteflies and aphids. At the gin, reduced ginning rates and poor operation can occur as a result of this honeydew-induced stickiness of cotton. At the textile mill, where machinery is designed to operate within very stringent material handling parameters, far more serious processing problems can occur. As a result, some cotton production areas are penalized monetarily because of their reputation for sticky cotton.

Cotton stickiness can be attributed to the presence of sugars on the fiber surface. Sugar is a colloquial term used to describe certain members of the class of compounds called carbohydrates. The sugars present on cotton fibers can be divided into two main types reflecting their origin: (1) physiological sugars and (2) sugars produced by feeding insects. Stickiness due to the droplets of entomological sugar are of major importance.

Identification of the stickiness of cotton at the gin, textile mill, or laboratory cannot be done quickly with conventional systems. The current methods of determining the sugar content and/or stickiness of cotton involve using laboratory methods that are not applicable to rapid or continuous, on-line measurements. One such conventional system is the Minicard test. The Minicard test is a mechanical method of testing for stickiness and was designated by the International Textile Manufacturers Federation (ITMF) as the reference method until 1994. The Minicard test, as utilized in North America, classifies cotton into four levels of stickiness; 0, 1, 2, and 3. On occasion, a stickiness level of 4 is assigned to unusually sticky samples by some users. A 10-g sample of cotton is processed through a miniature card (Minicard) and the degree of stickiness of the cotton on the steel delivery rolls is then rated subjectively. The results of the Minicard test are considered to correlate well with stickiness problems in the mill. However, the equipment is expensive and is time intensive in its operation. The honeydew group at the ITMF Bremen meeting in 1988, concluded that the Minicard was the best indicator of honeydew stickiness on cotton. In 1994, however, this same group decided to use the thermodetection method instead.

In the thermodetection method, a web of fiber (about 2.5 g) is placed between two sheets of aluminum foil on the bottom plate of a heating press. Pressure is briefly exerted on the top of the sheets using a heating plate at high temperature. A second, relatively longer pressure of a few minutes, is then exerted without heat after which the preparation is left to settle. The cotton web is then removed from the aluminum sheets, but the sticky spots adhere strongly and remain attached to the sheets. This method has certain advantages over the Minicard, and results seem to correlate well with the Minicard test. The thermodetector is compact and needs little maintenance; the test is simpler and less expensive than the Minicard, takes about 10 to 12 min/sample using one operator; and has the advantage that permanent records can be obtained in the form of aluminum foil sheets with attached spots.

Both the Minicard test and the thermodetection method are relatively slow, and expensive to perform. Neither test is suitable for continuous, on-line measurements. Therefore, there is a need in the art for a system for rapidly evaluating the level of stickiness of cotton that can be used for continuous, on-line measurements.

SUMMARY OF THE INVENTION

The present invention provides a system and method for determining the stickiness of agricultural solids, such as cotton. A first moisture measuring means measures resistance or capacitance of a sample of the agricultural solids to determine a reference moisture level. This first moisture measuring means may include a sensor array having a plurality of electrodes for measuring resistance and/or capacitance, a pressure sensor, and a temperature sensor. A second moisture measuring means based on infra-red (IR) is responsive to the presence of both moisture and sugars. This is used to determine a sugar-based moisture content in the sample. Processing means, such as a personal or desktop computer, is used to determine the stickiness of the sample by analyzing the variation between the reference and sugar-based moisture contents.

Testing of the sample is accomplished by its being pressed by a pressing means against the sensing or measuring surface of the moisture measuring means to a degree that ensures that an accurate measurement is made. The pressing means may be accomplished by any art-known means such as a paddle, a ram or any similar device actuated by means including hand and foot pressure.

A feature of the present invention, in addition to its supplying manual or desktop measurements, is its automatic and continuous provision of stickiness measurements for agricultural solids such as cotton. This may be accomplished at material handling facilities such as gins, grain or textile mills or laboratories. A further feature of the present invention is that the agricultural solid can be analyzed as it is traveling through a conduit such as in a gin or processing mill, without its having to be removed.

An advantage of the present invention is that it can be used at any stage of the processing of agricultural solids. For example, the system can be used to measure the stickiness of an agricultural product, such as cotton, as it is harvested, stored, moduled, ginned, graded, cleaned, or carded.

A further advantage of the present invention is that it is portable and easily adaptable for any gin configuration or cotton analysis system.

It is yet a further advantage of the present invention that it provides an accurate estimate of the stickiness of cotton during classification by the United States Department of Agriculture (USDA), Agricultural Marketing Service (AMS), as well as other organizations.

A still further advantage of the present invention is that it provides data regarding stickiness that allows the gin or processing mill to take corrective action to improve the final product. For example, in response to excessive stickiness as measured by the present invention, a gin or processing mill can apply chemical additives to reduce the sugar content.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE EMBODIMENTS

The invention may be beneficially employed for the measurement of the sugar content and its resultant stickiness of cotton, as well as other flowable agricultural solids such as grains (e.g., corn, wheat, rice, oats, etc.), legumes (e.g., soybeans and peanuts), seeds, nuts, and cellulosic products (e.g., wood chips). Flowable agricultural solids are defined as those which, while solid, are of such a particulate nature that they are amenable to harvest, transport, and processing in a continuous manner due to their possession of gross general flow characteristics. Details of the invention will be described with regard to processing cotton, although it may be similarly employed for other solids.

Figure 1:
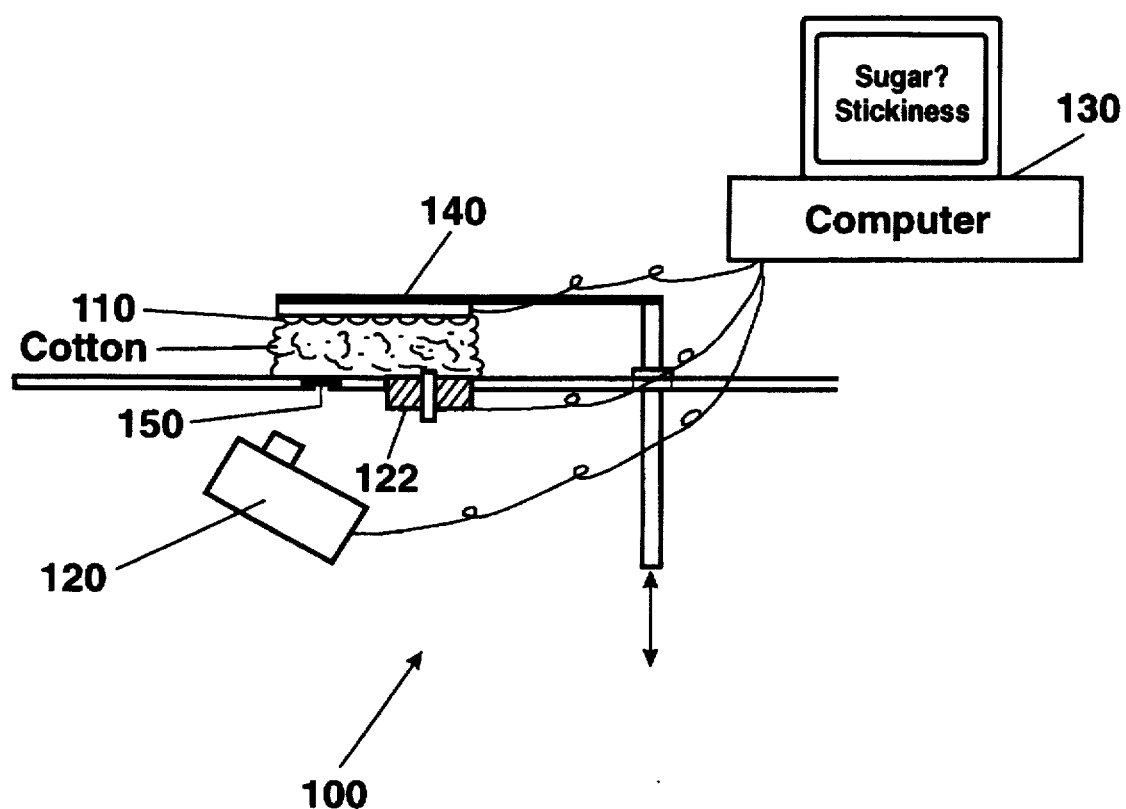
FIG. 1 shows an intermittent laboratory system of the present invention for determining stickiness of agricultural solids such as cotton.

In FIG. 1, the system of the present invention for determining the sugar content and its resultant stickiness of agricultural solids such as cotton is shown generally at 100. The system as shown in FIG. 1, includes three types of sensors for measuring the moisture content of the sample of cotton. The first type is a resistance moisture sensor 110. The electrical resistance of a material is correlatable with its moisture content. Therefore, measuring the resistance of the material provides a reference moisture level. This reference moisture level as measured by resistance moisture sensor 110 is not affected by the presence of sugars.

The second type of moisture sensor is a capacitance sensor 122, which like the resistance moisture sensor 110, is also unaffected by the presence of sugars. Any conventional capacitance moisture sensor known to one of skill in the relevant art can be used.

The third type of moisture sensor shown in FIG. 1 is an infrared moisture sensor 120. Any conventional infrared moisture sensor known to one of skill in the relevant art can be used. Examples of such include the infrared moisture sensors made by Infrared Engineering, Inc., or Moisture Systems Corp. Infrared sensor 120 is responsive to intermittent presence of sugars that may be located on the sample of cotton.

The moisture level of a sample of cotton as measured by infrared sensor 120, is reduced by the presence of sugars. As explained more fully in the examples below, this differential between the reference moisture level measured by resistance moisture sensor 110 or the capacitance sensor 122 and that of the sugar-based moisture content, as measured by the infrared sensor 120, provides a measure of the relative sugar content and stickiness of the sample.

As shown in FIG. 1, resistance moisture sensor 110 is mounted on a pressing means, shown generally at 140, that presses resistance moisture sensor 110 against the sample of cotton. This is done so that the sample of cotton presents a face of uniform cotton density against resistance moisture sensor 110. As used herein, the phrase "a face of uniform cotton (or agricultural solid) density" means that the face of the sample that is pressed against the measurement surface is sufficiently free of void space, so as to not markedly affect the measurement readings taken from the sample by an amount more than about 5%; this being accomplished by ensuring that no more than a ⅛" variance in the distance between the material surface and the measurement interface occurs. In other words, the sample is sufficiently compressed so that its flattened face is substantially occupied by cotton and impurities. This enables the moisture measuring sensors to make an accurate measurement.

The cotton sample shown in FIG. 1 is pressed up against resistance moisture sensor 110 and up against a glass lens or window 150 so as to form a face of uniform cotton density against both. The infrared measurement is made through this glass lens or window 150. The resistance and capacitance measurements are made by means of direct contact with the solid.

A computer or other processing means 130 is used to control the various components of system 100. Computer 130 may be used to trigger the sensors to take measurements, to control the movement of pressing means 140, to receive and process the measurement data, and to compute the stickiness of the cotton sample. A conventional desktop or personal computer can be used. Such a computer typically includes a processor, display, keyboard and memory storage.

Figure 2:
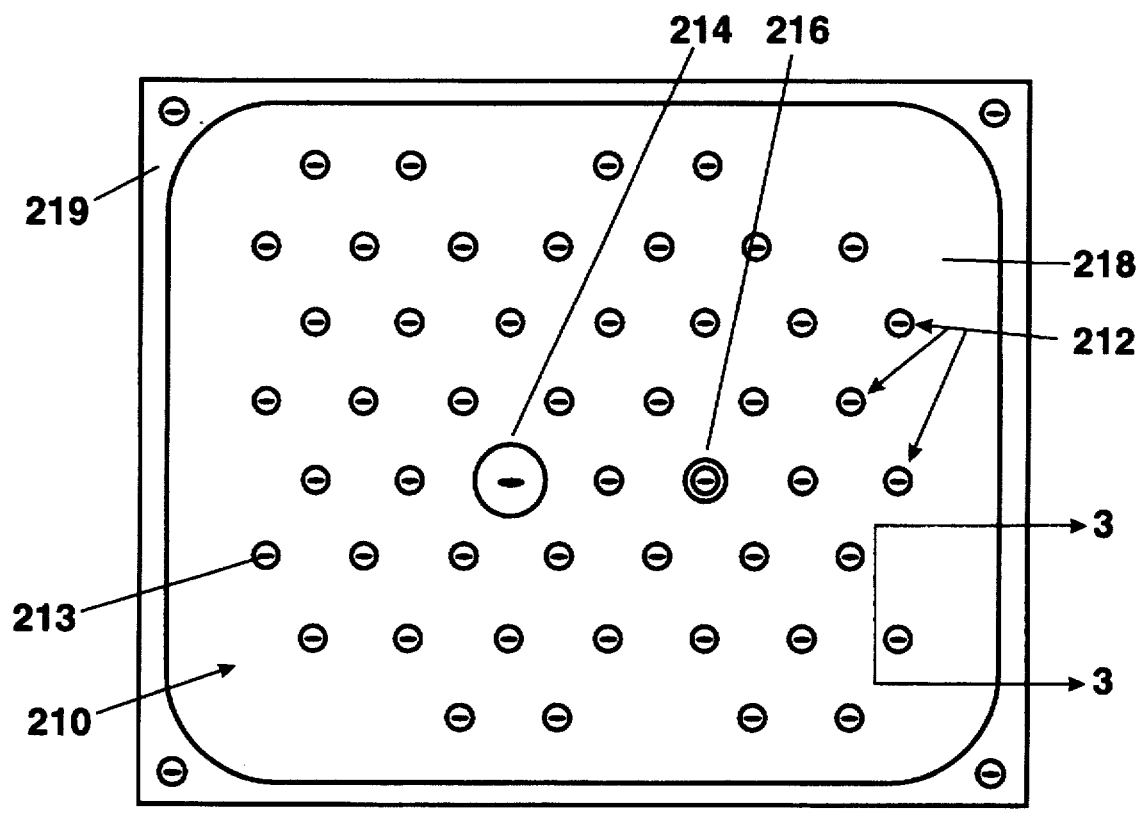
FIG. 2 shows a top view of a sensor array.

A particularly preferred resistance moisture measuring system is described in U.S. application Ser. No. 08/273,244 now U.S. Pat. No. 5,514,973; the entirety of which is incorporated herein by reference. A resistance moisture sensor array 210 is shown in FIG. 2. Sensor array 210 includes a plurality of electrodes 212. Electrodes 212 are preferably stainless steel, but other conductive material that is relatively inert in the atmosphere to which it is exposed, such as brass, could also be used. The electrodes are preferably configured in the form of multiple electrically and physically independent electrode pairs, each electrode pair forming a channel. One electrode of each of the pairs is electrically common and is maintained at a reference potential, being referred to herein as a "reference-potential electrode." The other electrode of the pair is referred to herein as a "measuring electrode."

Figure 3:
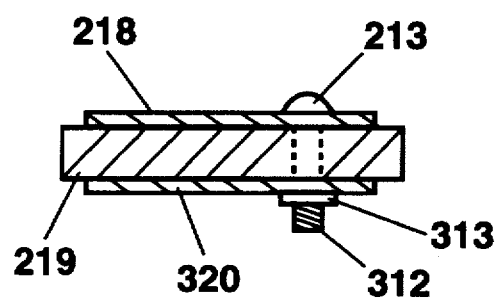
FIG. 3 shows a cross-section along line 3—3 in FIG. 2.

Electrode 212 includes a head 213 and a threaded portion 312 (see FIG. 3). Head 213 mounts against a plate 218. Plate 218 is preferably made from TEFLON™, but other materials which have very low conductance and which do not generate appreciable static electricity could also be used. Beneath plate 218 is a mounting plate 219. Mounting plate 219 is preferably made from plexiglass or other acrylic. However, other material having a very low conductance and structural strength could also be used. Alternatively, plate 218 and mounting plate 219 can be made from the same material.

As explained more fully below, sensor array 210, as shown in FIG. 2, also includes a pressure sensor 214. Pressure sensor 214 is used to determine when the sample has been sufficiently pressed against sensor array 210 to ensure accurate resistance measurements. Sensor array 210 also includes a temperature sensor 216. Temperature sensor 216 measures the temperature of the sample, and computer 130 then adjusts the resistance measurements to compensate for the temperature.

A cross-section of a portion of sensor array 210 is shown in FIG. 3. A ground plane 320 is disposed below mounting plate 219. Ground plane 320 is preferably made from aluminum and keeps all of the reference-potential electrodes at the same potential. Alternatively, the reference-potential electrodes could be connected by wires, a conductive film deposited on mounting plate 219, or other suitable method. Electrode 212 is secured to sensor array 210 via nut 313 that engages threaded portion 312.

Figure 4:
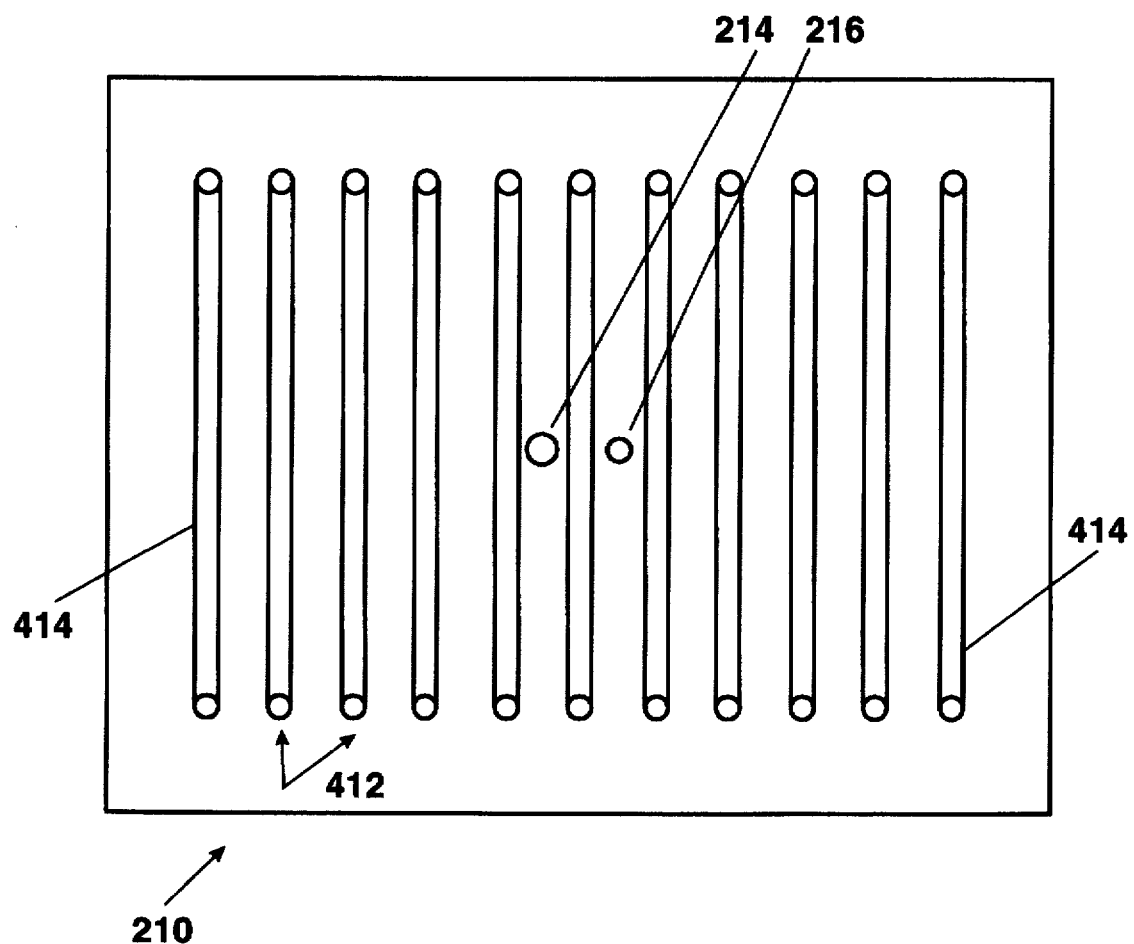
FIG. 4 shows an alternate embodiment of a sensor array that incorporates rod-shaped electrodes.

FIG. 4 illustrates an alternate embodiment of sensor array 210 that incorporates a plurality of rod-shaped electrodes 412. Electrodes 412 are also preferably configured as electrode pairs. Both outside electrodes 414 and every second electrode 412, are held at the reference voltage as reference-potential electrodes.

Consistent and repeatable measurement of material resistivity requires that a face of uniform density of the tested material is placed in contact with sensor array 210, window 150, or other measuring surface. Pressures of about 1 to about 6 psi on the surface of sensor array 210 are suitable for sufficiently compressing cotton to provide a cotton face of uniform density. When sufficiently compressed, the face of the cotton mass typically experiences a pressure of about 2 psi; and the mass will ordinarily be compressed to a thickness of about 0.5 inch.

The particular means of sample compression is not critical. The present invention may be used in conjunction with known sample capture and compression means, such as those taught in U.S. Pat. No. 5,087,120 and in U.S. Pat. No. 5,125,279. The entirety of both of the foregoing patents is incorporated herein by reference. These patents are directed to apparatuses that operate within the material flowstreams of cotton processing plants for the purpose of providing samples which present a face of uniform cotton density against a measuring surface used to analyze for properties including moisture content. Sample compression may be achieved by other, including manual, means.

Figure 5:
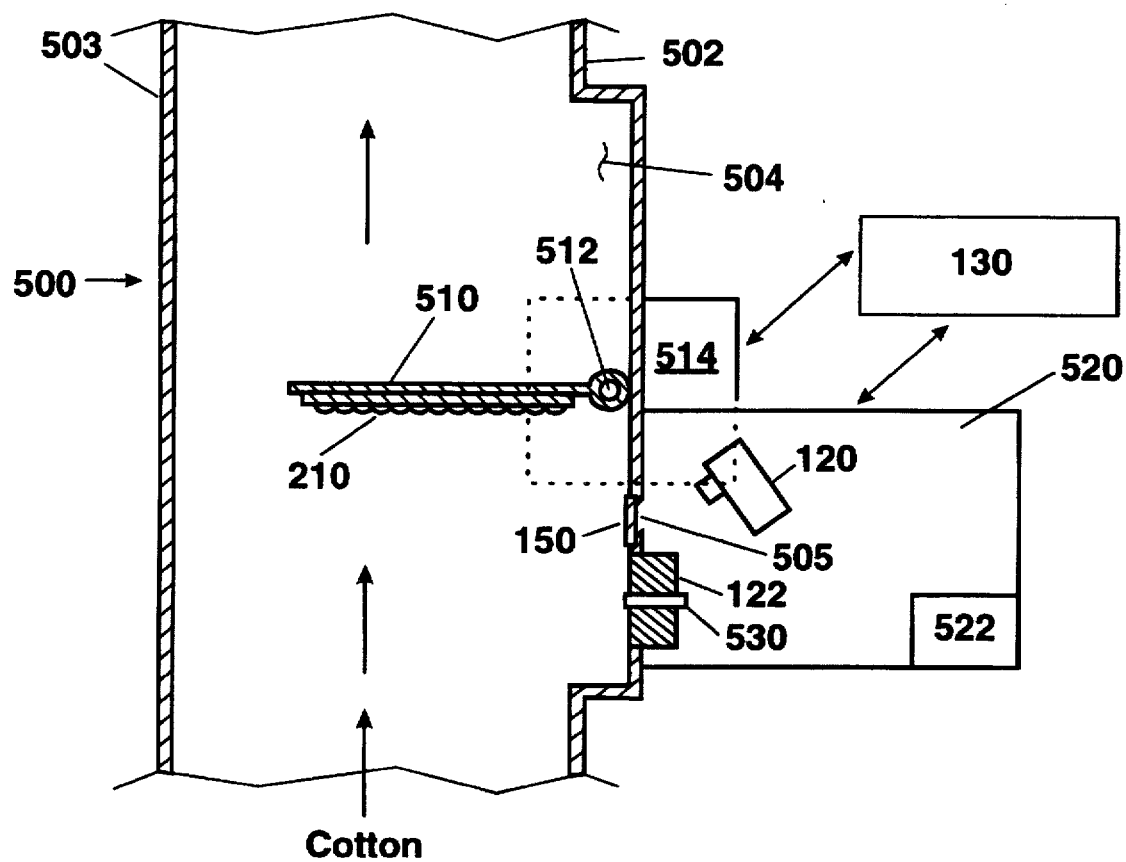
FIG. 5 shows the system of the present invention installed in a rectangular duct in a ginning system equipped with a paddle sampler.

FIG. 5 shows the system of the present invention installed in a rectangular duct in a ginning system equipped with a paddle sampler 510, such as that described in U.S. Pat. No. 5,087,120. Reference numeral 500 designates a typical rectangular duct in a ginning system, wherein the cotton is traveling upwardly toward, for example, a lint cleaner. The cotton usually is moving rapidly at speeds of about 1000–5000 feet per minute, typically about 1500 feet per minute for lint cotton, and about 4500 feet per minute for seed cotton.

Reference numerals 502 and 503 designate the front and back walls, respectively, of duct 500. The distance therebetween, or duct depth, typically is about 4–8 inches in the case of a lint duct; while full scale width typically is about 48–96 inches. For seed cotton, round ducts, having a diameter of about 12–24 inches, normally are used.

Provided in wall 502 is a recess 504. Positioned within recess 504 is a rotatable shaft 512 driven by a rotary actuator assembly 514. Paddle sampler 510 is positioned in its solids-capturing or -halting mode in FIG. 5, i.e., the paddle projects transversely into the duct. Sensor array 210 is attached to one side of paddle sampler 510 so that cotton can be compressed between sensor array 210 and window 150.

Figure 6:
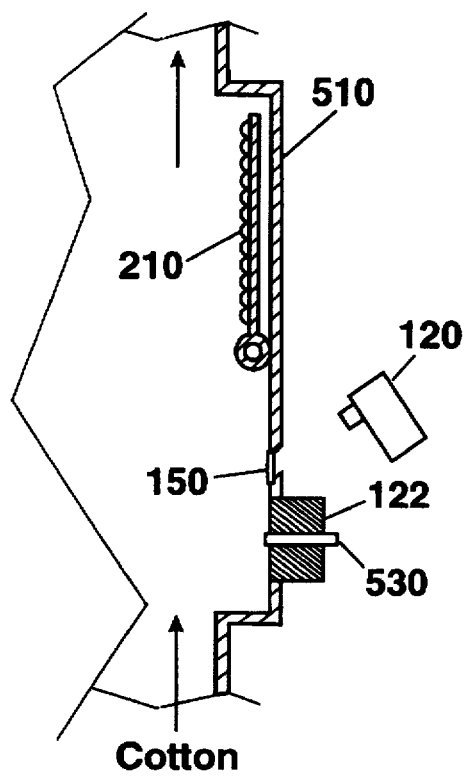
FIG. 6 shows the paddle sampler of FIG. 5 in a retracted position.
Figure 7:
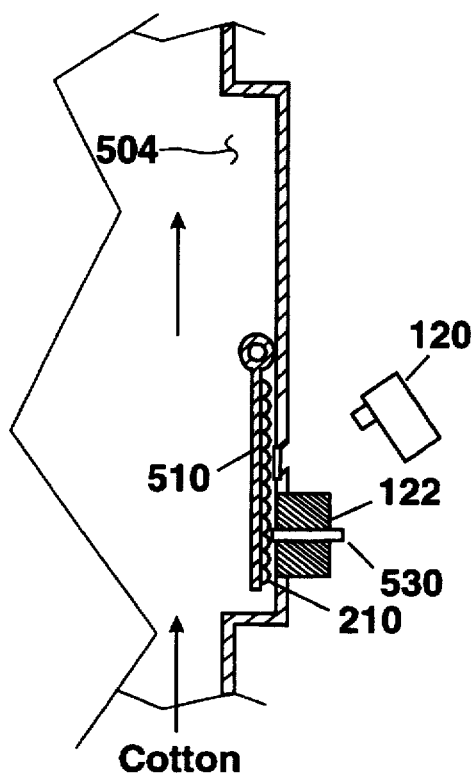
FIG. 7 shows the paddle sampler of FIG. 5 in a pressing position.

FIGS. 6 and 7 illustrate the pressing and retracted positions, respectively, of paddle sampler 510. In the pressing and retracted positions, paddle sampler 510 is positioned totally within recess 504 so as not to cause flow obstruction to cotton passing through the duct during compression or retraction.

Hydraulics, pneumatics, or electric motors may be employed to activate rotary actuator assembly 514, pneumatics being preferred. Dayton "Speedaire" model 2A121 is an exemplary pneumatic rotary actuator. In most instances, surface pressures of about 1 to 6 psi are suitable for sufficiently compressing the cotton so as to provide a cotton face of uniform density at sensor array 210. Under such pressure, the face of the cotton mass typically will experience a pressure of about 2 psi; and the mass ordinarily will be compressed to a thickness of about 0.5 inch.

Adjacent wall 502 is a housing 520 for the sensors and associated electronics for the measurement system of the present invention. Infrared moisture sensor 120 is disposed in housing 520. Capacitance moisture sensor 122 is positioned within housing 520 within an opening 505 in wall 502. Window 150 covers opening 505 to protect the sensors and circuitry installed in housing 520. Window 150 is transparent, thereby allowing the infrared measurements to be made.

Also disposed within housing 520 is time-delay circuitry 522. Time-delay circuitry 522 may be used to delay measurement by the various sensors until the sample is sufficiently compressed by paddle sampler 510. Time-delay circuitry 522 may include, for example, an off-the-shelf electronic time delay relay to trigger the sensors to take readings when compression of the cotton mass is at its maximum. For example, a relay with a timing range of about 0.1 to about 1.0 seconds may direct the compression cycle to start. The time delay relay may electrically signal a directional solenoid air valve which further signals rotary actuator assembly 514 to activate. An electrical signal is sent to computer 130 by the time delay relay about the same time as rotary actuator assembly 514 is directed to rotate paddle sampler 510 to define the precise time for computer 130 to take a reading. Sufficient time is allowed for rotary actuator assembly 514 to fully rotate paddle sampler 510 to the pressing position. This time, typically 1 second, is used to delay computer 130 from triggering the sensor readings until full rotation occurs. The time delay relay also allows a variable momentary pause after a proximity switch 817 (see FIG. 8) is activated, typically about 1 second, to ensure that computer 130 receives a stable reading before paddle sampler 510 begins its return to the retracted position.

A preferred means to trigger computer 130 may be provided by pressure sensor 214 in sensor array 210 or optionally a pressure sensor 530 installed in opening 505 as shown in FIG. 5. Pressure sensor 530 may be used in addition to, or instead of, pressure sensor 214 in sensor array 210. Pressure sensor 214 and pressure sensor 530 perform the same function. They measure the pressure produced as the sample is being compressed, i.e., pressed against sensor array 210, or against pressure sensor 530. The pressure measured by the pressure sensor is transmitted to computer 130 to determine when the sample is sufficiently pressed, i.e., when sufficient density is achieved to ensure accurate sensor measurements. Computer 130 then triggers the infrared, resistance, and/or capacitance sensors to take the measurements.

Figure 8:
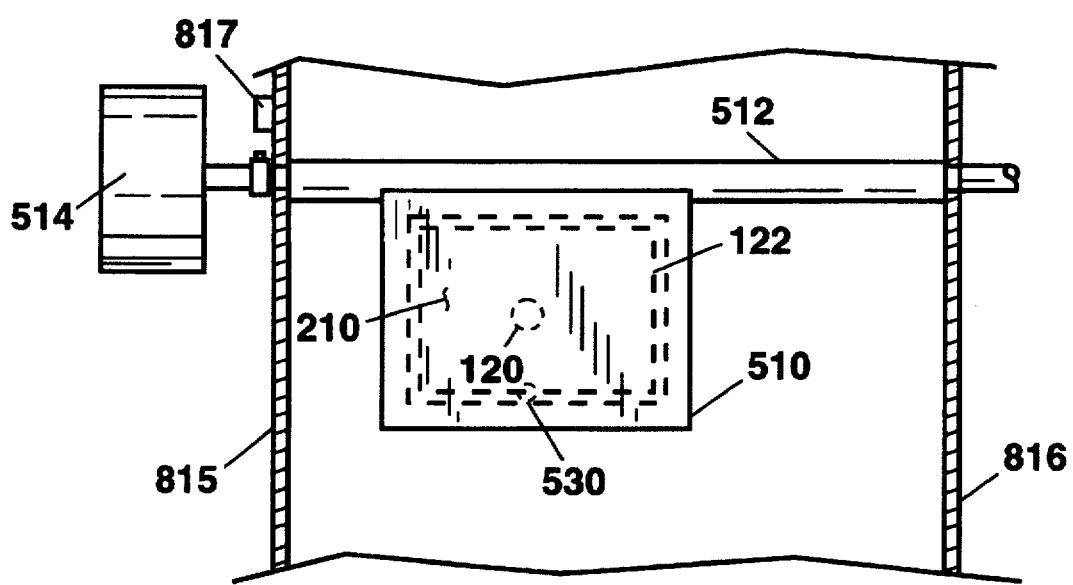
FIG. 8 shows a front view of the system of FIG. 5.
Figure 9:
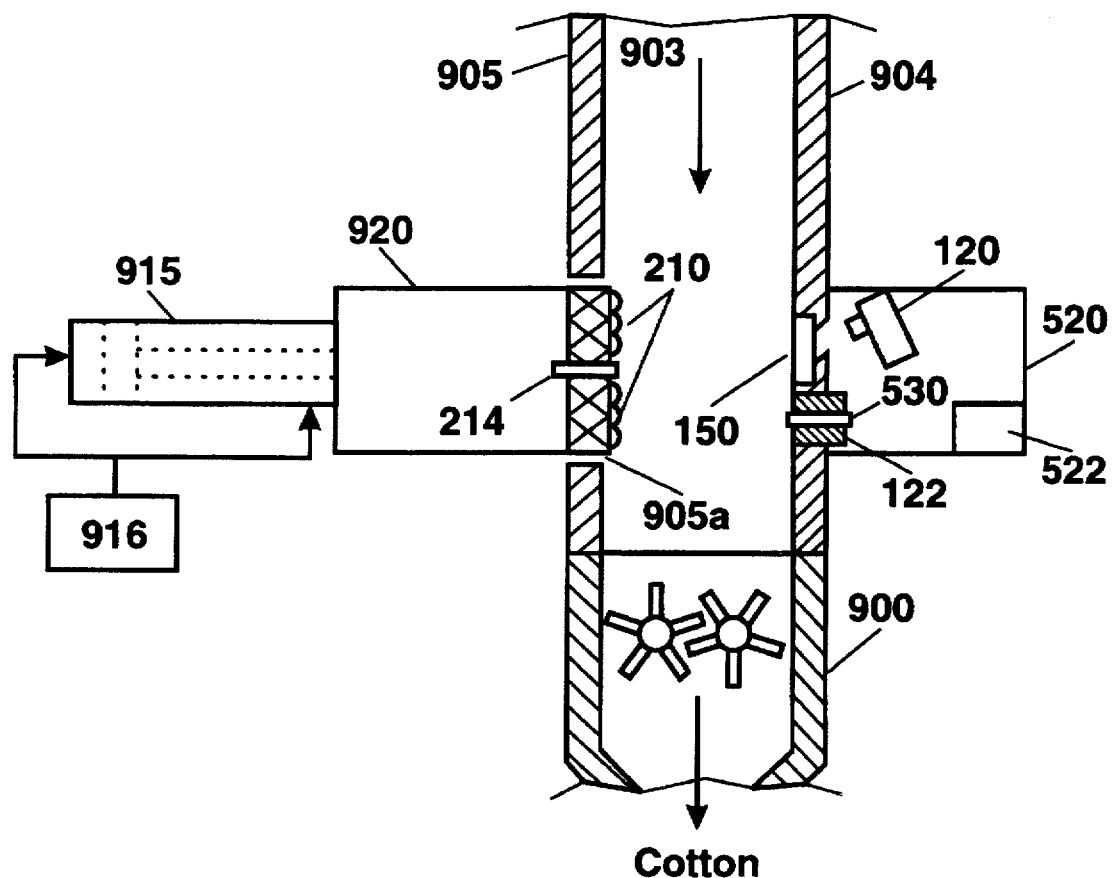
FIG. 9 shows the system of the present invention installed in a rectangular duct in a ginning system equipped with a ram sampler, with the ram sampler in a retracted position.

A front view of paddle sampler 510 in the pressing position is shown in FIG. 8. The side walls of duct 500 are identified by reference numerals 815 and 816. Proximity switch 817 is disposed on side wall 815, above rotary actuator assembly 514. Reference numerals 904 and 905 designate first and second opposing walls or surfaces, preferably the front and back walls of chute 900. Adjacent to wall 905 at opening 905a, directly opposite housing 520 and the associated sensors, is a conventional piston-cylinder assembly 915 fixed to a frame member (not shown), supplied with fluid pressure from a source 916. Assembly 915 is connected to ram sampler 920 that intermittently or cyclically displaces cotton from its downward pathway and compresses the displaced cotton against window 150. Sensor array 210 is attached to the end of ram sampler 920 so that cotton can be compressed between sensor array 210 and window 150.

Figure 10:
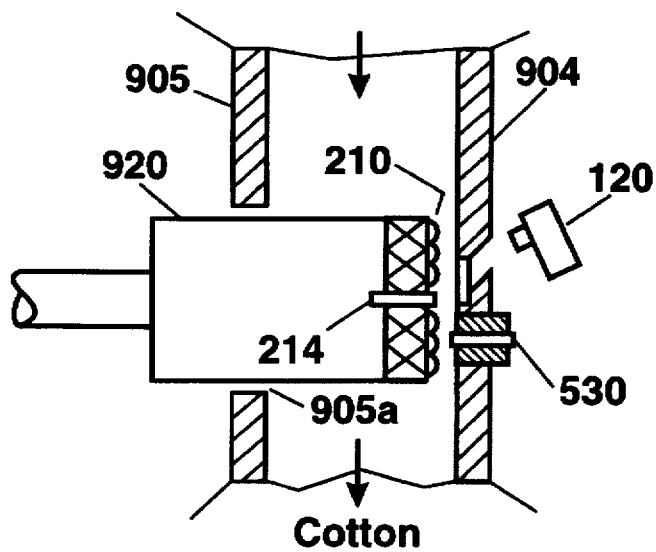
FIG. 10 shows the ram sampler of FIG. 9 in an extended pressing position.

Ram sampler 920 should be of sufficient length to traverse the distance between walls 904 and 905 and to have at least a part of ram sampler 920 lodged in opening 905a, even when fully extended, as shown in FIG. 10. In this manner, no cotton will be trapped behind ram sampler 920 during its retraction stroke. In addition, by maintaining at least part of ram sampler 920 within opening 905a during the entire operation, support is continuously provided for the ram.

During operation of the present invention, a sample of cotton to be analyzed or graded is captured by activating a sampler such as the paddle sampler or the ram sampler described above. The cotton sample is then pressed by the sampler to form a face of uniform density against sensor array 210 and window 150. The sensors, resistance moisture sensor 110, infrared moisture sensor 120, and capacitance sensor 122, are then triggered to take the measurements, and the data transmitted to computer 130 for processing.

Figure 11:
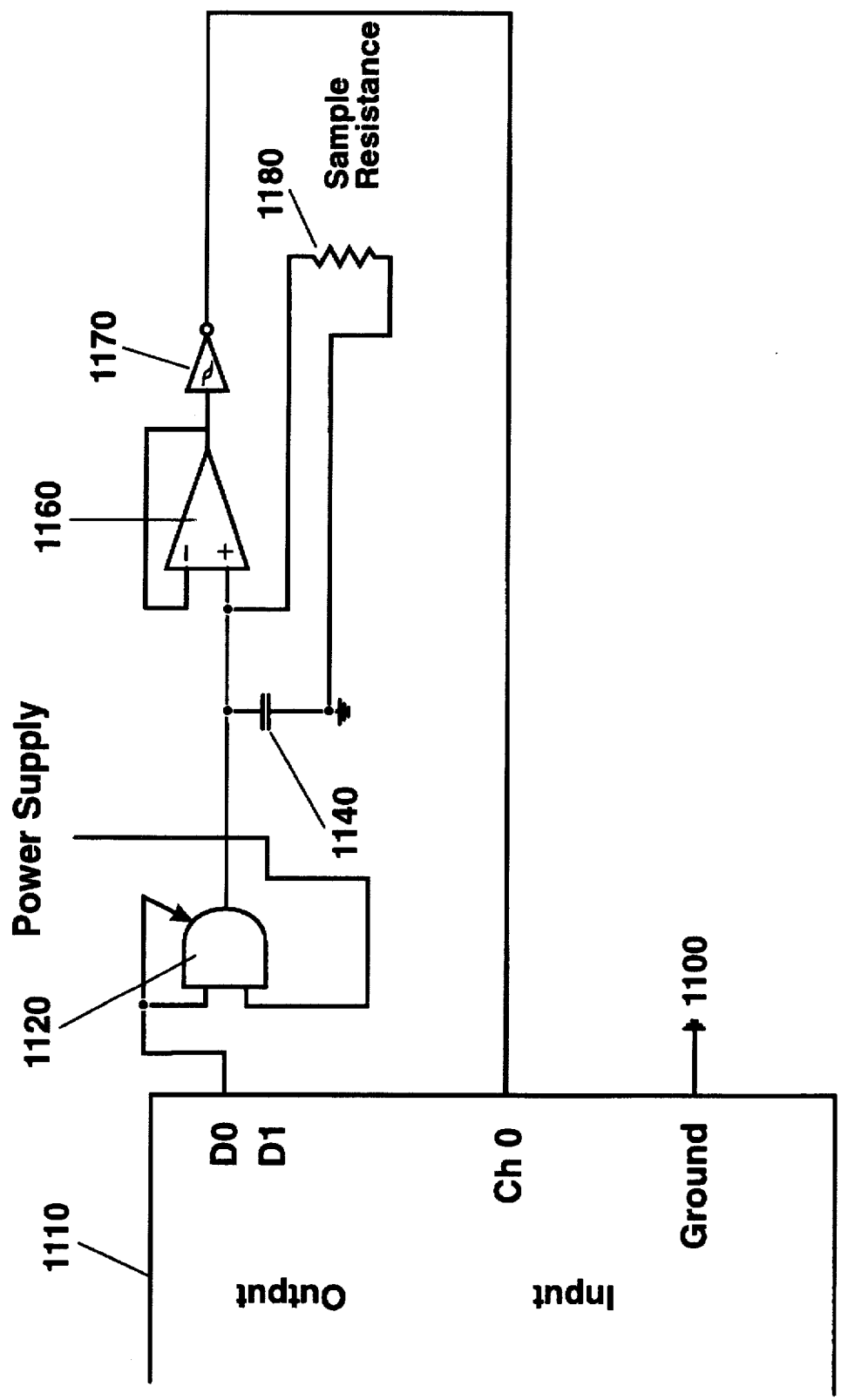
FIG. 11 shows a schematic of a circuit that can be used for converting resistance measure to moisture content.

A circuit 1100 that can be used for converting resistance measure to moisture content is shown in FIG. 11. Independent resistance measures are collected from each measuring electrode of sensor array 210. Circuit 1100 includes a charging gate 1120, controlled by a microprocessor 1110. The output voltage at gate 1120 goes high, charging capacitor 1140, and then the charging circuitry, gate 1120, assumes a high impedance state.

Circuit 1100 also includes a sensing amplifier (high impedance voltage follower) 1160 and a Schmitt trigger 1170. The sample resistance being measured (sample of which the moisture is to be sensed) is shown as sample resistance 1180. Sensing amplifier 1160 has a high input impedance to minimize discharge of capacitor 1140 through sensing amplifier 1160. Similarly, charging gate 1120 has low reverse leakage to minimize capacitor discharge. Capacitor 1140 thus discharges through sample resistance 1180, and Schmitt trigger 1170 determines when the discharge voltage is reduced to a predetermined level.

The length of time that the voltage across sample 1180 is high, after the charging circuitry assumes a high impedance state, is proportional to the sample resistance. This time delay is measured by microprocessor 1110. This time delay is then transmitted to computer 130 to convert to moisture content using known conversion or calibration equations, such as those described by Byler (American Society of Agricultural Engineers, Paper No. 923032; June 1992; and 1992 *Proceedings Beltwide Cotton Conference*, pp. 1389–1391; herein incorporated by reference).

Calculation of the moisture content (M) may also be achieved by using the equation:

$$M_n = A_n * ln(t_n) + B_n \quad (1)$$

where $M_n$=the moisture content measured by channel n, $t_n$=the time to discharge the capacitor measured on channel n, and $A_n, B_n$=coefficients determined by regression.

For applications where the temperature of the material to be tested is not constant, material temperature sensor 216 may be incorporated into the moisture measuring means, and readings therefrom supplied to computer 130 to adjust resistance readings for any temperature effect.

An alternate equation which may be used is:

$$M_n = A_n + (B_n - C_n/t_n)/t_n - D_n t_n \quad (2)$$

where $M_n$=the moisture content measured by channel n, $t_n$=the time to discharge the capacitor measured on channel n, and $A_n, B_n, C_n, D_n$=coefficients determined by regression.

After the moisture content for each channel (electrode pair) has been determined by either equations (1) or (2), the moisture content by channel is examined to see if it should be retained for further analysis.

The individual electrode-based moisture readings are then statistically analyzed by computer 130 and those with moisture values that fall outside preset parameters are culled. These values are readily determinable by one of ordinary skills in the art and will vary with the material being measured as well as the means by which it is being processed. One approach, is to keep all readings within a certain range (e.g., those between 5.0% and 9.0%), or keep all readings within a certain range of the expected mean (e.g., 7.5±1.5%). An additional approach, is to keep a running average of the mean square of the moisture readings for the different channels of the individual samples for all samples as the system analyzes data. All points within an estimated three standard deviations of the mean of the readings for that sample would be kept and the others discarded. The mean would then be taken of the remaining data and used as the estimate of the sample reference moisture level.

The sugar-based moisture content is determined by a near infrared device such as a near infrared photometric analyzer that does analyses of near infrared energy at fixed wavelengths of 1.9 and 1.4 microns. It operates on the principle that water molecules are not static, but vibrate. It takes energy to cause the vibrations, and some of the energy from the invisible light of the near infrared source is absorbed in a manner that is proportional to the number of water molecules whereas energy is not absorbed at other wavelengths. A reference wavelength that is not absorbed by water is used for comparison with the wavelength that is absorbed by water. The relationship between the absorption of energy at the two wavelengths is converted to an electrical signal which is transmitted to the host computer simultaneously with the electrical signals provided by other moisture measurement devices such as the resistance sensor. The electrical signals are calibrated to represent moisture levels.

Assessment of the stickiness of samples of material such as cotton may be accomplished with statistical approaches such as a procedure called "Discriminant Analysis" which computes various discriminant functions for classifying samples into categories. The performance of the functions can be evaluated by comparing the predicted classifications with the actual classifications and determining the error rate.

Threshold values for the different levels of stickiness can be determined by the use of functions in the form of:

Stickiness $0 = c_0 + a_0$ times (resistance moisture)+$b_0$ times (infrared moisture)

Stickiness $1 = c_1 + a_1$ times (resistance moisture)+$b_1$ times (infrared moisture)

Stickiness $2 = c_2 + a_2$ times (resistance moisture)+$b_2$ times (infrared moisture)

Stickiness $3 = c_3 + a_3$ times (resistance moisture)+$b_3$ times (infrared moisture)

Stickiness 4=$c_4$+$a_4$ times (resistance moisture)+$b_4$ times (infrared moisture)

where:

$a_{1-4}$, $b_{1-4}$, and $c_{1-4}$ are different numerical values associated with the functions.

In order to assess the stickiness of materials such as cotton, a set of readings for a sample is analyzed using the aforementioned functions, and the highest numerical result is associated with the classification of 4, the next highest with 3, with this process being repeated for each of the progressively lower classification numbers. Typical values for these variables are:

$c_0$=−623.27, $a_0$=209.26 and $b_0$=−38.99

$c_1$=−664.05, $a_1$=224.35 and $b_1$=−49.54

$c_2$=−615.79, $a_2$=214.81 and $b_2$=−46.23

$c_3$=−695.29, $a_3$=228.03 and $b_3$=−48.85

$c_4$=−775.37, $a_4$=240.86 and $b_4$=−51.65 with creation of alternate values from different data sets being within the purview of one skilled in the art.

The following examples show how the reference moisture level, measured by resistance moisture sensor 110, is combined with the measurements from infrared moisture sensor 120 to determine the stickiness of a sample.

EXAMPLE 1

Seven samples of cotton with unknown growth locations, but having different levels of stickiness, were obtained form USDA-ARS at Clemson, S.C., and combined with three samples from the West/Southwest that were obtained from USDA-ARS at Las Cruces, N. Mex. These samples were subdivided into trashy seed cotton, precleaned seed cotton, and ginned lint. In addition, three samples of clean, low sugar, nonsticky cotton from the Stoneville area were added for a total of 13 samples.

Comparison of the infrared and resistance readings (Table 1) from these samples indicated that cottons were usually sticky if the resistance-based moisture exceeded the infrared-based moisture by 0.8%. Further analysis of these data using the Discriminate Analysis procedure by the Statistical Analysis System (SAS) indicated that these 13 samples could be divided into categories of 0, 1, 2, 3, and 4 regardless of the natural sugar by using the resistance and infrared methods. For each of the samples, two readings were taken on a side of the cotton and the sample turned over and two additional readings taken. These data were averaged to produce one data point. When this procedure was replicated on different days for a total of three times, 12 of the 13 samples received similar classifications to those assigned by the Minicard test.

TABLE 1

Moisture Measurements by Resistance, Infrared, Capacitance, Methods, and Natural Sugar Contents for Study 1

| Sample | Moisture (%) | | | Reducing | Stickiness, | Predicted |
|---|---|---|---|---|---|---|
| (No.) | R* | IR† | C‡ | Sugar↑ | Minicard# | Stickiness** |
| 1 | 7.3 | 5.5 | 6.8 | 0.9 | 0 | 1†† |
| 2 | 7.5 | 6.2 | 6.9 | 0.3 | 1 | 1 |
| 3 | 6.8 | 6.2 | 6.7 | 0.6 | 0 | 0 |
| 4 | 7.3 | 6.0 | 6.9 | 0.3 | 1 | 1 |
| 5 | 7.3 | 6.5 | 6.7 | 0.3 | 0 | 0 |

TABLE 1-continued

Moisture Measurements by Resistance, Infrared, Capacitance, Methods, and Natural Sugar Contents for Study 1

| Sample | Moisture (%) | | | Reducing | Stickiness, | Predicted |
|---|---|---|---|---|---|---|
| (No.) | R* | IR† | C‡ | Sugar↑ | Minicard# | Stickiness** |
| 6 | 7.1 | 5.4 | 6.6 | 0.7 | 3 | 3 |
| 7 | 7.2 | 5.9 | 6.9 | 0.4 | 1 | 1 |
| 8 | 7.1 | 6.8 | 6.9 | ‡‡ | 0 | 0 |
| 9 | 7.3 | 6.9 | 7.0 | ‡‡ | 0 | 0 |
| 10 | 7.6 | 7.1 | 7.2 | ‡‡ | 0 | 0 |
| 11 | 8.1 | 6.5 | 6.7 | ‡‡ | 4 | 4 |
| 12 | 8.1 | 6.5 | 6.7 | ‡‡ | 4 | 4 |
| 13 | 7.9 | 6.5 | 6.6 | ‡‡ | 4 | 4 |

*Resistance based method.
†Infrared-based method.
‡Capacitance-based method.
↑Natural plant sugars.
0 = not sticky, 1 = slightly sticky, 2 = moderately sticky, 3 = sticky, and 4 = very sticky
††Indicates misclassification. This sample was correctly identified when moisture measurements by infrared, resistance and oven techniques were used.
‡‡Data not available.
**Based on moisture measurements by infrared and resistance technique.

EXAMPLE 2

Twenty-nine additional samples grown in different locations across the Cotton Belt were obtained from the Fiber Quality Research section of Cotton Incorporated at Raleigh, N.C., and combined with the original 13 samples of Example 1, to which three additional samples from the Stoneville area, including lint and seed cotton, were added. These samples contained natural sugar contents ranging from 0.3 to 1.5% and stickiness levels determined by the Minicard to be from 0 to 4.

Using the same test procedure as was used for Example 1, 74% of the nonsticky samples were placed into the correct category (Table 2). For the sticky samples, 67% of the level 1 samples, 83% of the level 2 samples, and 100% of the level 3 and level 4 stickiness samples were similarly classified. As a result of the lower rate of correlation for the level 1 samples, the sample handling methods were evaluated. It appeared that the rigorous handling of the cotton on numerous occasions caused it to be somewhat lumpy and irregular, and prevented it from presenting a uniform, smooth surface to the sensor even under compression. Consequently, in replication four, the handling techniques were modified so that only the top and bottom of the sample were measured and the sample was not opened to allow the interior to be measured. This procedure appeared to slightly improve the ability to predict sample stickiness. For replication 5, each of the samples was processed through one additional stage of lint cleaning in order to smooth and comb them, and perhaps return the samples closer to their original condition. This procedure improved the correlation between the two methods for both the zero and level 2 of stickiness, but reduced such for the level 1 stickiness.

For replication six, the procedure was further modified. Eight readings were taken on a side by moving the sample about 1 inch between each reading, in order to ensure that a spot of insect sugar was considered directly. The sample was then turned over and eight readings made on the other side. This procedure appeared to increase the prediction of the level 0 sample by two percentage points. Results from six replications were combined into one database to determine if the prediction accuracy changed as a result of the different handling techniques. With the combined database, 65, 27, 80, 100% and 100% of the samples were similarly classified as 0, 1, 2, 3 and 4 stickiness levels, respectively. Thus, it appears that repeated handling of the samples impacts the effectiveness of the device. The Minicard classification of the samples was then changed to either sticky or nonsticky without regard to level of stickiness. With this approach, 78% of the nonsticky samples and 85% of the sticky samples were similarly identified.

TABLE 2

Moisture (Resistance, Infrared, and Capacitance), Sugar, Minicard Stickiness, and Predicted Stickiness for Example 2

| Sample | Moisture (%) | | | Reducing Sugar | | Predicted |
|---|---|---|---|---|---|---|
| (No.) | R† | IR‡ | C§ | % | Minicard | Stickiness⊤ |
| 2 | 7.2 | 5.9 | 6.8 | 0.3 | 1 | 1 |
| 4 | 7.2 | 5.9 | 6.9 | 0.3 | 1 | 1 |
| 5 | 7.2 | 6.4 | 6.7 | 0.3 | 0 | 0 |
| 6 | 7.0 | 5.8 | 6.7 | 0.7 | 3 | 3 |
| 7 | 7.1 | 5.8 | 6.8 | 0.4 | 1 | 1 |
| 8 | 7.1 | 6.9 | 6.9 | # | 0 | 0 |
| 9 | 7.1 | 6.6 | 7.0 | # | 0 | 0 |
| 10 | 7.4 | 6.9 | 7.0 | # | 0 | 0 |
| 11 | 7.7 | 6.4 | 6.7 | # | 4 | 4 |
| 12 | 7.9 | 6.3 | 6.8 | # | 4 | 4 |
| 13 | 8.0 | 7.2 | 6.7 | # | 4 | 4 |
| 14 | 6.8 | 5.9 | 6.6 | 1.0 | 0 | 2** |
| 15 | 7.1 | 6.2 | 6.8 | 1.0 | 1 | 1 |
| 16 | 6.8 | 5.8 | 6.7 | 1.0 | 2 | 2 |
| 17 | 6.9 | 6.4 | 6.8 | 0.7 | 1 | 1 |
| 18 | 7.0 | 6.4 | 6.7 | 0.8 | 2 | 2 |
| 19 | 6.9 | 5.4 | 6.7 | 1.4 | 2 | 2 |
| 20 | 6.8 | 5.9 | 6.6 | 0.8 | 1 | 2** |
| 21 | 6.8 | 6.0 | 6.7 | 1.1 | 1 | 2** |
| 22 | 6.9 | 6.0 | 6.6 | 0.7 | 3 | 3 |
| 23 | 7.0 | 6.5 | 6.8 | 0.2 | 2 | 0** |
| 24 | 6.6 | 5.9 | 6.7 | 0.7 | 0 | 2** |
| 25 | 6.8 | 6.2 | 6.7 | 0.6 | 1 | 2** |
| 26 | 7.0 | 6.4 | 6.8 | 0.2 | 0 | 1** |
| 27 | 7.4 | 6.3 | 6.7 | 0.8 | 2 | 2 |
| 28 | 6.8 | 6.3 | 6.6 | 0.2 | 2 | 2 |
| 29 | 7.0 | 6.6 | 6.7 | 0.2 | 0 | 0 |
| 30 | 7.1 | 6.4 | 6.8 | 1.0 | 2 | 3** |
| 31 | 7.3 | 6.0 | 6.8 | 0.7 | 3 | 3 |
| 32 | 6.9 | 6.4 | 6.8 | 0.2 | 2 | 2 |
| 33 | 6.7 | 6.0 | 6.6 | 0.7 | 0 | 0 |
| 34 | 7.0 | 6.6 | 6.8 | 0.2 | 1 | 0** |
| 35 | 7.2 | 6.2 | 6.9 | 0.6 | 3 | 3 |
| 36 | 7.1 | 6.0 | 6.8 | 0.6 | 2 | 2 |
| 37 | 7.1 | 6.4 | 6.8 | 0.7 | 0 | 0 |
| 38 | 6.9 | 7.2 | 6.7 | 0.2 | 1 | 0 |
| 39 | 6.8 | 6.4 | 6.7 | 0.6 | 1 | 0 |
| 40 | 7.0 | 6.5 | 6.7 | 0.6 | 0 | 1** |
| 41 | 6.7 | 6.2 | 6.6 | 0.6 | 2 | 2 |
| 42 | 7.3 | 6.2 | 6.8 | 0.1 | 3 | 3 |
| 43 | 7.3 | 7.1 | # | # | 0 | 0 |
| 44 | 7.0 | 6.9 | 6.8 | # | 0 | 0 |
| 45 | 6.8 | 7.0 | 7.2 | # | 0 | 0 |

*Samples 1 and 3 are same samples as example 1 and insufficient cotton was available for example 2.
†Resistance-based method.
‡Infrared-based method.
§Capacitance-based method.
⊤Based on moisture measurements by the infrared and resistance techniques.
Data not available.
**Indicates misclassification.

EXAMPLE 3

Seed cotton samples from examples 1 and 2 above were isolated into separate databases and analyzed. Only two levels of stickiness were available based on Minicard readings from lint taken from the seed cotton—0 and 4. For the eight samples of seed cotton (four sticky and four nonsticky samples, data not shown), 100% of the samples were similarly identified by the apparatus. This increased precision was likely due to the fact the insect sugar droplets were still intact on the surface of the cotton and had not been broken up, combed, and blended as would occur during normal ginning and lint cleaning operations.

The present invention provides an accurate estimate of the stickiness of cotton during the official classification (grading for market purposes) by the USDA, AMS. It can also be used in the textile industry to measure the stickiness of cotton and synthetics and allow control of the manufacturing process. It can also be used to measure the stickiness of cotton in the field, in storage, and while modules of cotton are being constructed. It can also be used to measure the sugar content of cotton after it is harvested from the cotton plant and is being transported pneumatically or gravitationally into a storage container mounted on a mechanical harvester. The invention could also be used to measure the sugar content of other similar materials such as grain, seed, wood chips, etc.

While various embodiments of the present invention have been described above, it should be understood that they have been presented by way of example only, and not limitation. For example, the invention may be used in conjunction with a standard High Volume Instrument (HVI) color and trash meter which is used to establish color and trash parameters for cotton grown throughout the world. As another example, the system can be configured to be "hand-held," with a mechanical spring pressing the sample against the sensors. The electronics can be configured to be battery-operated, making the system of the present invention easily transportable. Thus, the breadth and scope of the present invention should not be limited by any of the above-described exemplary embodiments, but should be defined only in accordance with the following claims and their equivalents.

What is claimed is:

1. A system for determining the stickiness of agricultural solids, comprising:
   first moisture measuring means for determining a reference moisture level in a sample of agricultural solids, wherein said first moisture measuring means is not responsive to the presence of sugars in the agricultural solids;
   second moisture measuring means for determining a sugar-based moisture content in the sample, wherein said second moisture measuring means is responsive to the presence of sugars in the agricultural solids; and
   processing means coupled to said first moisture measuring means and to said second moisture measuring means for comparing said reference moisture level to said sugar-based moisture content to thereby determine the stickiness of the sample.

2. The system of claim 1, wherein said first moisture measuring means comprises a sensor array that comprises a plurality of electrically conductive electrodes, and wherein said processing means converts measures from said electrodes into said reference moisture level.

3. The system of claim 2, further comprising:
   pressing means for pressing the sample to form a face of uniform agricultural solids density against said sensor array.

4. The system of claim 2, wherein said sensor array further comprises:
   a temperature sensor for measuring a temperature of the sample, wherein said processing means adjusts the results of said first and second moisture measuring means to compensate for the temperature of the sample.

5. The system of claim 3, wherein said sensor array further comprises:

a pressure sensor for measuring a pressure produced as said pressing means presses the sample against said sensor array.

6. The system of claim 1, wherein said first moisture measuring means comprises a resistance or capacitance sensor.

7. The system of claim 3, wherein said second moisture measuring means comprises an infrared sensor.

8. The system of claim 7, further comprising: delay means for delaying measurement by said first moisture measuring means and said second moisture measuring means until the sample is sufficiently pressed against said sensor array by said pressing means.

9. The system of claim 3, wherein said pressing means comprises:

a rotatable paddle; and means for rotating said paddle between a retracted position and a pressing position.

10. The system of claim 3, wherein said pressing means comprises:

a moveable ram; and means for moving said ram between a retracted position and a pressing position.

11. A method for determining the stickiness of a sample of agricultural solids, comprising:

(A) measuring a reference moisture content of the sample using a measuring means which is not responsive to the presence of sugars in the sample;

(B) measuring a sugar-based moisture content of the sample using moisture measuring means responsive to the presence of sugars in the sample; and (C) comparing said reference moisture content to said sugar-based moisture content to thereby determine the stickiness of the sample.

12. The method of claim 11, wherein the reference moisture content measuring means of step (A) comprises a resistance or capacitance sensor.

13. The method of claim 12, further comprising: adjusting the reference moisture content determined by step (A) to compensate for temperature of the sample.

14. The method of claim 11, wherein the measurement of the sugar-based moisture content in step (B) is performed using an infrared sensor.

15. The method of claim 12, further comprising in Step (A):

pressing the sample to form a face of uniform agricultural solids density against said reference moisture content measuring means.

16. The method of claim 15, wherein steps (A) and (B) are performed after the sample is sufficiently pressed against said reference moisture content measuring means.

* * * * *